United States Patent [19]
Cordi et al.

[11] Patent Number: 5,482,933
[45] Date of Patent: Jan. 9, 1996

[54] PHOSPHONOMETHYL-IMIDAZO[1,2-A] PYRIMIDINE-2-CARBOXYLIC ACID COMPOUNDS FOR TREATMENT OF NEUROTOXIC INJURY

[75] Inventors: Alexis A. Cordi, Suresnes, France; Eric T. Sun, San Diego, Calif.

[73] Assignee: G. D. Searle & Co., Chicago, Ill.

[21] Appl. No.: 140,370

[22] Filed: Oct. 21, 1993

Related U.S. Application Data

[60] Division of Ser. No. 982,819, Nov. 30, 1992, Pat. No. 5,302,586, which is a continuation-in-part of Ser. No. 810,242, Dec. 19, 1991, abandoned.

[51] Int. Cl.[6] ................ A61K 31/675; A61K 31/505
[52] U.S. Cl. .................................. 514/81; 514/80
[58] Field of Search ................ 514/81, 80, 258; 544/244, 232, 252, 253

[56] References Cited

U.S. PATENT DOCUMENTS

| | | | |
|---|---|---|---|
| 4,532,243 | 7/1985 | Tully | 514/258 |
| 4,636,502 | 1/1987 | Spitzer | 514/249 |
| 4,657,899 | 4/1987 | Rzeszotarski et al. | 514/120 |
| 4,918,064 | 4/1990 | Cordi et al. | 514/114 |

OTHER PUBLICATIONS

S. M. Rothman et al, *Annals of Neurology*, 19 (2), (1986).
M. N. Perkins et al, *Neuroscience Lett.*, 23, 333 (1981).
J. Davies et al, *Neuroscience Lett.*, 21, 77 (1981).
K. Matoba et al, "Structural Modification of Bioactive Compound II. Syntheses of Aminophosphonic Acids", *Chem. Pharm. Bull.*, 32 (10), 3918–3925 (1984).
D. E. Murphy et al, *J. Pharmacol. Exp. Ther.*, 240 (3), 778–784 (1987).

*Primary Examiner*—Shailendra Kumar
*Attorney, Agent, or Firm*—Timothy Keane

[57] ABSTRACT

A class of phosphonomethyl-imidazo[1,2-a]pyrimidine-2-carboxylic acid compounds is described for treatment to reduce neurotoxic injury associated with anoxia or ischemia which typically follows stroke, cardiac arrest, hypoglycemia or perinatal asphyxia. The treatment includes administration of a compound of this class alone or in a composition in an amount effective as an antagonist to inhibit excitotoxic actions at major neuronal excitatory amino acid receptor sites. Compounds of most interest are those of the formula:

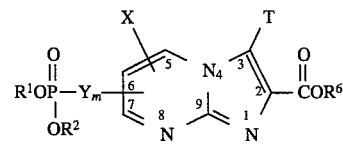

wherein each of $R^1$, $R^2$ and $R^6$ is independently selected from hydrido, alkyl, allyl, cycloalkyl, cycloalkylalkyl, phenyl and benzyl; wherein $Y_m$ is —$CH_2$— or —$CH_2$—$CH_2$—; where m is one; wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio and amino; or a pharmaceutically-acceptable salt thereof.

11 Claims, No Drawings

5,482,933

PHOSPHONOMETHYL-IMIDAZO[1,2-A] PYRIMIDINE-2-CARBOXYLIC ACID COMPOUNDS FOR TREATMENT OF NEUROTOXIC INJURY

RELATED APPLICATION

This is a Divisional of application Ser. No. 07/982,819 filed Nov. 30, 1992, now U.S. Pat. No. 5,302,586, which is a continuation-in-part of U.S. application Ser. No. 07/810, 242 filed Dec. 19, 1991, abandoned.

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest, hypoglycemia or perinatal asphyxia.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman et al, *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.*, 23, 333 (1981); and J. Davies et al, *Neuroscience Lett.*, 21, 77 (1981)]. In particular, compounds such as 2-amino-4-(2-phosphonomethyl-phenyl)butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.*, 32, (10) 3918–3925 (1984)].

An analogue of 2-amino-7-phosphonoheptanoic acid, namely 3-(2-carboxypiperazin-4-yl)propyl-1-phosphonic acid [CPP], has been reported as a potent and selective NMDA antagonist in an evaluation of CPP binding to rat brain hippocamal tissue [D. E. Murphy et al, *J. Pharmacol. Exp. Ther.*, 240 (3), 778–784 (1987)].

U.S. Pat. No. 4,657,899 to Rzeszotarski et al, which issued, describes a class of w-[2-phosphonoalkylenyl)phenyl]2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-[2-(2-phosphonoethyl)phenyl]-2-aminopropanoic acid.

U.S. Pat. No. 4,918,064 to Cordi et al, which issued 17 Apr. 1990, describes a class of phosphonomethylphenylglycine compounds for treatment to reduce neurotoxic injury associated with anoxia or ischemia which typically follows stroke, cardiac arrest or perinatal asphyxia.

Several classes of imidazopyrimidine compounds are known having various pharmaceutical uses. For example, U.S. Pat. No. 4,532,243 to Tully, which issued 30 Jul. 1985, describes a series of 5/7-alkyithio/alkoxy-imidazo[1,2-a] pyrimidines as anxiolymic agents. U.S. Pat. No. 4,636,502 to Spitzer, which issued 13 Jan. 1987, describes a series of 2-phenyl-imidazo[1,2-a]pyrimidines for use as inotropic agents and vasodilators.

DESCRIPTION OF THE INVENTION

Control of neuropathological processes and the neurodegenerative consequences thereof in a subject is provided by treating the subject susceptible to neurotoxic injury with an anti-excitotoxic effective amount of a compound characterized in having activity as an antagonist at a major neuronal excitatory amino acid receptor site, such as the NMDA receptor site. Such antagonist compounds may be selected from a class of imidazo[1,2-a]pyrimidine compounds defined by Formula I:

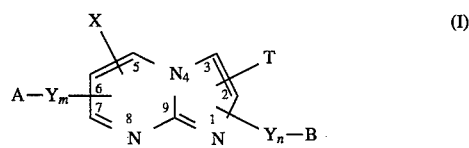

wherein A is selected from

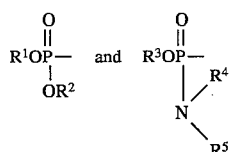

wherein B is selected from

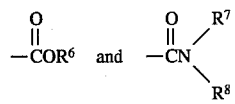

wherein each of $R^1$ through $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

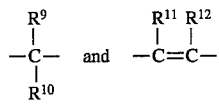

with the proviso that the total number of carbon atoms in each of $Y_m$ or $Y_n$ cannot exceed twenty carbon atoms; wherein each of $R^9$ and $R^{10}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein $R^9$ and $R^{10}$ may be taken together to form oxo or exomethylene; wherein each of $R^{11}$ and $R^{12}$ is independently selected from hydrido, alkyl, haloalkyl, phenyl, hydroxyalkyl and alkoxyalkyl; wherein each of m and n is a number independently selected from zero to four, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

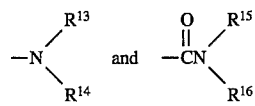

wherein each of $R^{13}$, $R^{14}$, $R^{15}$ and $R^{16}$ is independently selected from hydrido, alkyl and phenyl;
or a pharmaceutically-acceptable salt thereof.

within the class of compounds of Formula I, there is a first sub-class consisting of compounds of Formula II

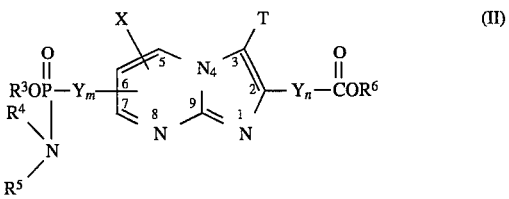

wherein each of $R^3$, $R^4$, $R^5$ and $R^6$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

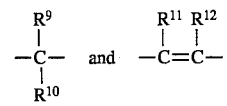

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein $R^9$ and $R^{10}$ may be taken together to form oxo or exomethylene; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the tetrahydroimidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

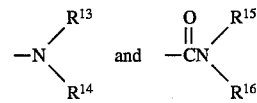

wherein each of $R^{13}$, $R^{14}$, $R^{15}$ and $R^{16}$ is independently selected from hydrido, alkyl and phenyl;
or a pharmaceutically-acceptable salt thereof.

Specific compounds of particular interest within Formula II are compounds, and their pharmaceutically-acceptable salts, of the group of compounds consisting of
ethyl 5-[(ethoxyphosphonamide)methyl]-imidazo[1,2-a]pyrimidine-2-carboxylate;
5-(phosphonamidemethyl)-imidazo[1,2 -a]pyrimidine-2-carboxylic acid;
ethyl 6-[(ethoxyphosphonamide)methyl]-imidazo[1,2-a]-pyrimidine-2-carboxylate;
6-(phosphonamidemethyl)-imidazo[1,2-a]pyrimidine-2-carboxylic acid;
ethyl 7-[(ethoxyphosphonamide)methyl]-imidazo[1,2-a]pyrimidine-2-carboxylate;
7-(phosphonamidemethyl)-imidazo[1,2-a]pyrimidine-2-carboxylic acid;

ethyl 6-chloro-5-[(ethoxyphosphonamide)methyl]-imidazo[1,2-a]pyrimidine-2-carboxylate;
6-chloro-5-(phosphonamidemethyl)-imidazo[1,2-a]pyrimidine-2-carboxylic acid;
ethyl 7-chloro-5-[(ethoxyphosphonamide)methyl]-imidazo[1,2-a]pyrimidine-2-carboxylate;
7-chloro-5-(phosphonamidemethyl)-imidazo[1,2-a]pyrimidine-2-carboxylic acid;
ethyl 5-(ethoxyphosphonamide)-imidazo[1,2-a]pyrimidine-2-carboxylate;
ethyl 5-ethoxyphosphonamide)-imidazo[1,2-a]pyrimidine-2-carboxylate, monohydrochloride;
5-phosphonamide-imidazo[1,2-a]pyrimidine-2-carboxylic acid; ethyl 5-[2-(ethoxyphosphonamide)-E-ethenyl]-imidazo[1,2-a]pyrimidine-2-carboxylate;
5-(2-phosphonamide-E-ethenyl)-imidazo[1,2-a]pyrimidine-2-carboxylic acid; and
5-(2-phosphonamideethyl)-imidazo[1,2-a]pyrimidine-2-carboxylic acid.

Within the class of compounds of Formula I, there is a second sub-class consisting of compounds of Formula III

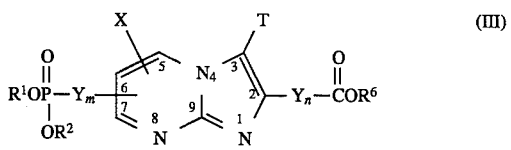

wherein each of $R^1$, $R^2$ and $R^6$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

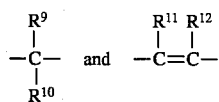

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein $R^9$ and $R^{10}$ may be taken together to form oxo or exomethylene; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

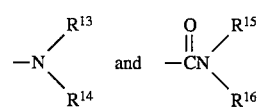

wherein each of $R^{13}$, $R^{14}$, $R^{15}$ and $R^{16}$ is independently selected from hydrido, alkyl and phenyl;

or a pharmaceutically-acceptable salt thereof.

Specific compounds of particular interest within Formula III are compounds, and their pharmaceutically-acceptable salts, of the group of compounds consisting of
ethyl 5-[(diethoxyphosphinyl)methyl]-imidazo[1,2-a]pyrimidine-2-carboxylate;
5-(phosphonomethyl)-imidazo[1,2-a]pyrimidine-2-carboxylic acid;
ethyl 6-[(diethoxyphosphinyl)methyl]-imidazo[1,2-a]pyrimidine-2-carboxylate;
6-(phosphonomethyl)-imidazo[1,2-a]pyrimidine-2-carboxylic acid;
ethyl 7-[(diethoxyphosphinyl)methyl]-imidazo[1,2-a]pyrimidine-2-carboxylate;
7-(phosphonomethyl)-imidazo[1,2-a]pyrimidine-2-carboxylic acid;
ethyl 6-chloro-5-[(diethoxyphosphinyl)methyl]-imidazo[1,2-a]pyrimidine-2-carboxylate;
6-chloro-5-(phosphonomethyl)-imidazo[2-a]pyrimidine-2-carboxylic acid;
ethyl 7-chloro-5-[(diethoxyphosphinyl)methyl]-imidazo[1,2-a]pyrimidine-2-carboxylate;
7-chloro-5-(phosphonomethyl)-imidazo[1,2-a]pyrimidine-2-carboxylic acid;
ethyl 5-(diethoxyphosphinyl)-imidazo[1,2-a]pyrimidine-2-carboxylate;
ethyl 5-diethoxyphosphinyl)-imidazo[1,2-a]pyrimidine-2-carboxylate, monohydrochloride;
5-phosphono-imidazo[1,2-a]pyrimidine-2-carboxylic acid; ethyl 5-[2-(diethoxyphosphinyl)-E-ethenyl]-imidazo[1,2-a]pyrimidine-2-carboxylate;
5-(2-phosphono-E-ethenyl)-imidazo[1,2-a]pyrimidine-2-carboxylic acid; and
5-(2-phosphonoethyl)-imidazo[1,2-a]pyrimidine-2-carboxylic acid.

within the class of compounds of Formula I, there is a third sub-class consisting of compounds of Formula IV

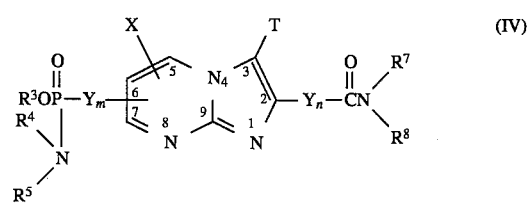

wherein each of $R^3$, $R^4$, $R^5$, $R^7$ and $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula $$-\underset{\underset{R^{10}}{|}}{\overset{\overset{R^9}{|}}{C}}- \quad \text{and} \quad -\overset{\overset{R^{10}}{|}}{C}=\overset{\overset{R^{12}}{|}}{C}-$$

with the proviso that the total number of carbon atoms in each of $Y_m$ or $Y_n$ cannot exceed ten carbon atoms; wherein each of $R^9$ and $R^{10}$ is independently selected from hydrido, alkyl cycloalkyl, halo, haloalkyl, hydroxy, hydroxyalkyl, alkoxy, alkoxyalkyl and alkanoyl; wherein $R^9$ and $R^{10}$ may be taken together to form oxo or exomethylene; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio, $$-\underset{\underset{R^{14}}{\diagdown}}{\overset{\overset{R^{13}}{\diagup}}{N}} \quad \text{and} \quad -\underset{\underset{R^{16}}{\diagdown}}{\overset{\overset{O}{\|}}{C}N}\overset{R^{15}}{\diagup}$$

wherein each of $R^{13}$, $R^{14}$, $R^{15}$ and $R^{16}$ is independently selected from hydrido, alkyl and phenyl;

wherein each of $R^3$, $R^4$, $R^5$, $R^7$ and $R^8$ is independently selected from hydrido, alkyl, allyl, cycloalkyl, cycloalkylalkyl, phenyl and benzyl;

or a pharmaceutically-acceptable salt thereof.

Specific compounds of particular interest within Formula IV are compounds, and their pharmaceutically-acceptable salts, of the group of compounds consisting of 5-[(ethoxyphosphonamide)methyl]-imidazo[1,2-a]pyrimidine-2-carboxamide;

5-(phosphonamidemethyl)-imidazo[1,2-a]pyrimidine-2-carboxamide;

6-[(ethoxyphosphonamide)methyl]-imidazo[1,2-a]pyrimidine-2-carboxamide;

6-(phosphonamidemethyl)-imidazo[1,2-a]pyrimidine-2-carboxamlde;

7-[(ethoxyphosphonamide)methyl]-imidazo[1,2-a]pyrimidine-2-carboxamide;

7-(phosphonamidemethyl)-imidazo[1,2-a]pyrimidine-2-carboxamide;

6-chloro-5-[(ethoxyphosphonamide)methyl]-imidazo[1,2-a]pyrimidine-2-carboxamide;

6-chloro-5-(phosphonamidemethyl)-imidazo[1,2-a]pyrimidine-2-carboxamide;

7-chloro-5-[(ethoxyphosphonamide)methyl]-imidazo[1,2-a]pyrimidine-2-carboxamide;

7-chloro-5-(phosphonamidemethyl)-imidazo[1,2-a]pyrimidine-2-carboxamide;

5-(ethoxyphosphonamide)-imidazo[1,2-a]pyrimidine-2-carboxamide;

5-ethoxyphosphonamide)-imidazo[1,2-a]pyrimidine-2-carboxamide, monohydrochloride;

5-phosphonamide-imidazo[1,2-a]pyrimidine-2-carboxamide;

5-[2-(ethoxyphosphonamide)-E-ethenyl]-imidazo[1,2-a]pyrimidine-2-carboxamide;

5-(2-phosphonamide-E-ethenyl)-imidazo[1,2-a]pyrimidine-2-carboxamide; and 5-(2-phosphonamideethyl)-imidazo[1,2-a]pyrimidine-2-carboxamide.

Within the class of compounds of Formula I, there is a fourth sub-class consisting of compounds of Formula V $$\text{(V)}$$

wherein each of $R^1$, $R^2$, $R^7$ and $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula $$-\underset{\underset{R^{10}}{|}}{\overset{\overset{R^9}{|}}{C}}- \quad \text{and} \quad -\overset{\overset{R^{11}}{|}}{C}=\overset{\overset{R^{12}}{|}}{C}-$$

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydro, by, hydroxyalkyl, alkoxy, alkoxyalkyl and alkanoyl; wherein $R^9$ and $R^{10}$ may be taken together to form oxo or exomethylene; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio, $$-\underset{\underset{R^{14}}{\diagdown}}{\overset{\overset{R^{13}}{\diagup}}{N}} \quad \text{and} \quad -\underset{\underset{R^{16}}{\diagdown}}{\overset{\overset{O}{\|}}{C}N}\overset{R^{15}}{\diagup}$$

wherein each of $R^{13}$, $R^{14}$, $R^{15}$ and $R^{16}$ is independently selected from hydrido, alkyl and phenyl;

or a pharmaceutically-acceptable salt thereof.

Specific compounds of particular interest within Formula V are compounds, and their pharmaceutically-acceptable salts, of the group of compounds consisting of 5-[(diethoxyphosphinyl)methyl]-imidazo[1,2-a]pyrimidine-2-carboxamide;

5-(phosphonomethyl)-imidazo[1,2-a]pyrimidine-2-carboxamide;

6-[(diethoxyphosphinyl)methyl]-imidazo[1,2-a]pyrimidine-2-carboxamide;

6-(phosphonomethyl)-imidazo[1,2-a]pyrimidine-2-carboxamide;

7-[(diethoxyphosphinyl)methyl]-imidazo[1,2-a]pyrimidine-2-carboxamide;

7-(phosphonomethyl)-imidazo[1,2-a]pyrimidine-2-carboxamide; 6-chloro-5-[(diethoxyphosphinyl)methyl]-imidazo[1,2-a]pyrimidine-2-carboxamide;

6-chloro-5-(phosphonomethyl)-imidazo[1,2-a]pyrimidine-2-carboxamide;

7-chloro-5-[(diethoxyphosphinyl)methyl]-imidazo[1,2-a]pyrimidine-2-carboxamide;

7-chloro-5-(phosphonomethyl)-imidazo[1,2-a]pyrimidine-2-carboxamide;

5-(diethoxyphosphinyl)-imidazo[1,2-a]pyrimidine-2-carboxamide;

5-diethoxyphosphinyl)-imidazo[1,2-a]pyrimidine-2-carboxamide, monohydrochloride;

5-phosphono-imidazo[1,2-a]pyrimidine-2-carboxamide;

5-[2-(diethoxyphosphinyl)-E-ethenyl]-imidazo[1,2-a]pyrimidine-2-carboxamide;

5-(2-phosphono-E-ethenyl)-imidazo[1,2-a]pyrimidine-2-carboxamide; and 5-(2-phosphonoethyl)-imidazo[1,2-a]pyrimidine-2-carboxamide.

The term "hydrido" denotes a single hydrogen atom (H). This hydrido group may be attached, for example, to an oxygen atom to form a hydroxyl group; or, as another example, one hydrido group may be attached to a carbon atom to form a >C- group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon amoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing from one to about ten carbon atoms.

specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I would be useful in control of neuropathological processes and the neuro-degenerative consequences thereof by administering a therapeutically-effective amount of a compound of Formula I to a subject in need of such control or treatment. A compound of Formula I would be useful alone, or in a composition containing one or more pharmaceutical excipients, for neuro-protective purposes such as for controlling or treating chronic or acute neurotoxic injury or brain damage resulting from a neuro-degenerative disease. Compounds of Formula I would be particularly useful for treating neurotoxic injury which follows periods of anoxia or hypoxia producing ischemia typically associated with stroke, cardiac arrest, hypoglycemia or perinatal asphyxia. The phrase "therapeutically-effective amount" of a compound of Formula I is defined as that amount of compound which produces an efficacious response in a subject afflicted with or susceptible to a neuro-degenerative disease.

In Formula I, as well as in Formulae II–V defining sub-sets of compounds within Formula I, there is shown an imidazo[1,2-a]pyrimidine ring system. Within the six-membered ring portion of this ring system, there are substitutable positions at the 5-, 6- and 7-ring positions. In each of Formulae I–V, there is a requirement for attachment of an acidic moiety at one of the 5-, 6- or 7-ring positions. This acidic moiety may be provided by a carboxylic acid or phosphorus-containing acid, or by the amide, ester or salt derivatives of such acids which when hydrolyzed would provide the acidic moiety. It is preferred that the acidic moiety be attached to the ring position through an alkylene group such as —CH$_2$— or —CH$_2$CH$_2$—. Favored positions for attachment of the acidic moiety are the 5- and 7-ring positions. The most favored position for attachment of the acidic moiety is at the 5-ring position. An X substituent, selected as defined above, may be attached at one or more of the 5-, 6- or 7-ring positions not occupied by the acidic moiety.

Also included in the family of compounds of Formula I are isomeric forms including diastereoisomers, including enantiomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitmric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylgluca-mine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–III, wherein the R and V substituents are as defined for Formula I, above, except where further noted.

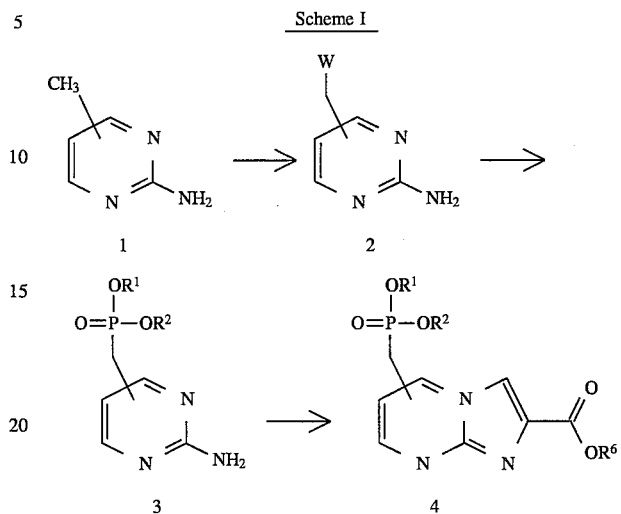

Scheme I

In Scheme I, there is shown a method to synthesize the products of the invention which starts with functionalization of the methyl radical of 2-amino-4-methyl pyrimidine or 2-amino-5-methyl pyrimidine (1). This operation can be conducted either by halogenation or oxidation or by any method deemed to transform the methyl group into a —CH$_2$—W residue (2) where W stands for a good leaving group such as, for instance, an halogen atom (Cl, Br, I) or a sulfonate ester (tosylate, mesylate, etc). Most of the time, the process will be multistep, as for example, the methyl can be oxidized into the carboxylic acid, which can be reduced to the corresponding alcohol which in turn can be reacted with a sulfonyl chloride to give the desired sulfonate ester. It could be advantageous to protect the amino function during the transformation of the methyl group, for instance when bromination of 2-amino-4-methyl pyrimidine is carried out with N-bromosuccinimide (NBS) bromination occurred not only on the methyl group but also on the position 5 of the aromatic ring. This reaction can be prevented by deactivation of the aromatic ring through acylation of the nitrogen by groups such as t-butyloxycarbonyl, acetyl, pivaloyl, or phthalyl. The product 2 is then reacted with a trialkylphosphite in an Arbuzov reaction or with a metallic salt of a dialkylphosphite leading to the synthesis of intermediate 3. The cyclization of 3 in the presence of ethyl-3-bromopyruvate lead to isomers which can be separated either by chromatography or by fractional crystallization. In the case the aromatic ring has been brominated at an earlier step, the halogen can be reduced by hydrogen gas, in basic media in the presence of palladium on carbon. The phosphonic and carboxylic ester functions can be selectively hydrolyzed by trimethylsilylhalide and one equivalent of NaOH am room temperature, respectively.

Scheme II

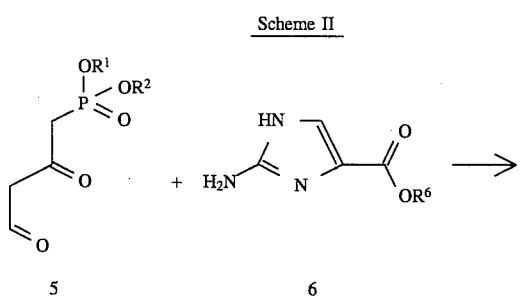

In Scheme II, there is shown a method to prepare Compound 7 by reacting 4-dialkylphosphono-3-keto-butanal (5) with a 2-amino-imidazole carboxylic ester 6. Two isomers are formed but the desired isomer will be the more abundant one. Separation of the two products can be achieved by chromatography or fractional crystallization.

Scheme III

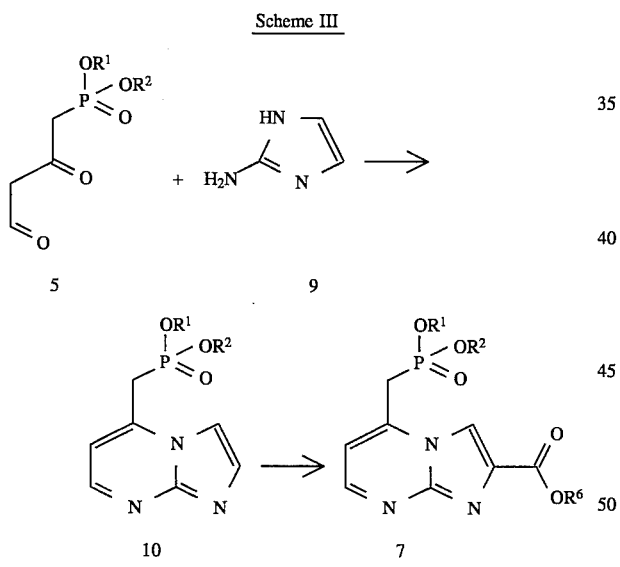

In Scheme III, there is shown a method to prepare Compound 7 by reacting the aldehyde 5 with 2-amino-imidazole 9 which will lead to the formation of only one product 10. Treatment of this product with a strong base such as lithium diisopropylamine or potassium t-butylate leads to the intermediate anion which can be acylated by $CO_2$, a chloroformate or a pyrocarbonate.

The following working Examples show detailed descriptions of the methods of preparation of compounds of Formula I. These detailed preparations fall within the scope of, and serve to exemplify, the above described General Synthetic Procedures which form part of the invention. These Examples are presented for illustrative purposes only and are not intended as a restriction on the scope of the invention. All parts are by weight unless otherwise indicated. In Schemes IV and V, there are shown respectively, specific methods for making compounds of the invention as described in more detail in Examples 1 and 2, which follow.

Scheme IV (Preparation of Example #1 Compound)

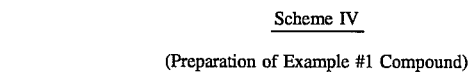

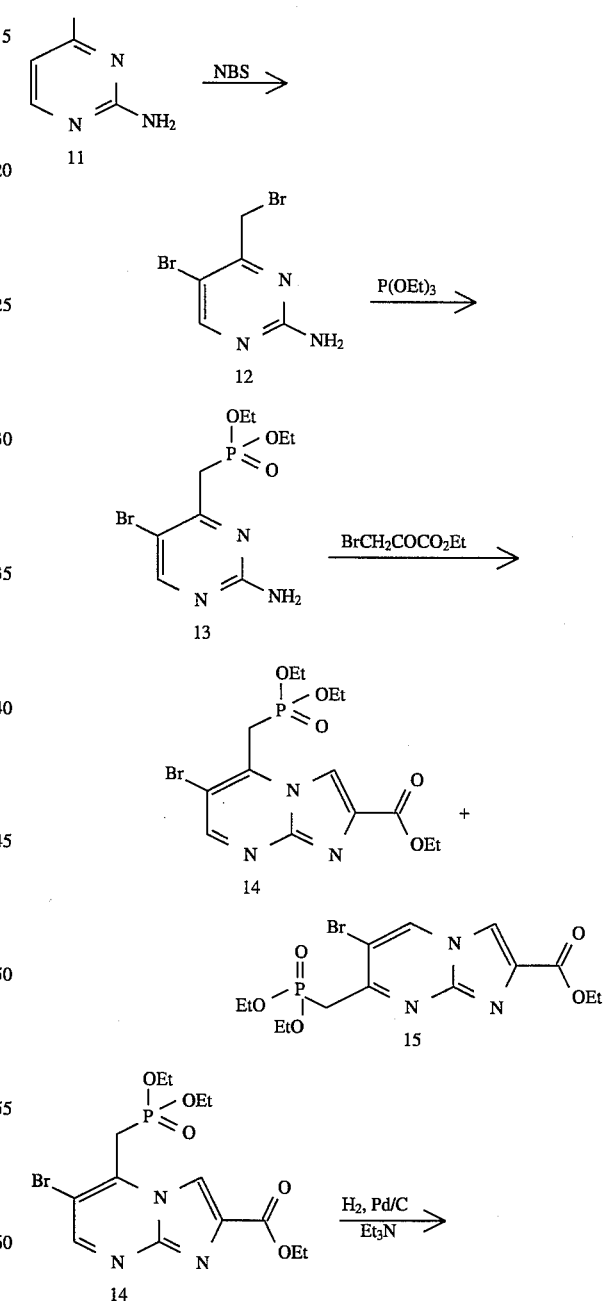

-continued
Scheme IV

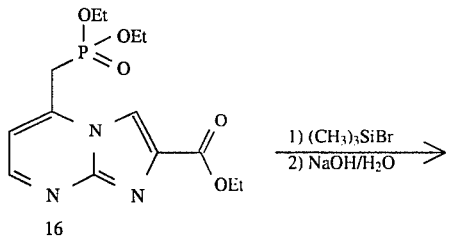

OH
|  /OH
P
‖ O

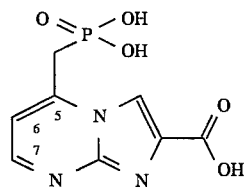

EXAMPLE 1

5-Phosphonomethyl-imidazo[1,2-a]pyrimidine-2-carboxylic acid (17)]

Step 1:

Synthesis of 2-Amino-5-bromo-4-(diethylphosphonomethyl)-pyrimidine (13)

2-Amino-4-methylpyrimidine (5 g, 0.046 mole) was brought to reflux for 24 hours in carbon tetrachloride (50 mL) in the presence of N-bromosuccinimide (NBS, 17.8 g, 0.1 mole) and AIBN (50 mg, 0.0003 mole). TLC (SiO₂, CH₂Cl₂-95/EtOH-5) indicated that only bromination of the aromatic ring took place. More NBS (17.8 g, 0.1 mole) is added and the reflux continued for 20 more hours. The solid was then filtered, washed twice with carbon tetrachloride (50 mL), the solvent was evaporated under reduced pressure. Triethylphophite (50 mL) was added and the solution brought to reflux for one hour. The excess triethylphosphite was evaporated under reduced pressure and the brown residue was purified through silicagel chromatography eluting with CH₂Cl₂-95/EtOH-5. A colorless oil was obtained.

Step 2:

Synthesis of Ethyl-6-bromo-5-(diethylphosphonomethyl)-imidazo[1,2-a]pyrimidine-2-carboxylic ester (14)

2-Amino-5-bromo-4-(diethylphosphonomethyl)-pyrimidine (0.5 g, 1.7 mmole) was suspended in an ethanolic solution of ethyl bromopyruvate (250 μL, 2 mmole in 45 mL). The suspension was stirred at room temperature overnight and then brought to reflux for two hours. The solvent was evaporated under reduced pressure, water was added and the solution was made basic by the addition of sodium bicarbonate. The aqueous phase was extracted with dichloromethane (3×20 mL), the organic phase was dried over potassium carbonate and evaporated under reduced pressure. The two isomers were separated on a silicagel chromatography column eluted with CH₂Cl₂-97/EtOH-3. The desired isomer 14 had the shorter retention time. The structure of 14 was confirmed by X-ray crystallographic analysis.

Step 3:

Synthesis of Ethyl-5-(diethylphosphonomethyl)-imidazo[1,2-a]pyrimidine-2-carboxylic ester (17)

Ethyl-6-bromo-5-(diethylphosphonomethyl)-imidazo[1,2-a]pyrimidine-2-carboxylic ester (90 mg, 0.2 mmole) was introduced in a round-bottom flask with ethanol (35 mL), triethylamine (100 μL) and Pd on Carbon (5%, 30 mg). The hydrogen buret and round-bottom flask were evacuated, filled with hydrogen and the reduction mixture was stirred at room temperature until gas absorption stopped. The catalyst was filtered through a celite bed, rinsed with ethanol and the solvent was evaporated under reduced pressure. Sodium bicarbonate was added to the residue which was extracted with dichloromethane, dried over potassium carbonate. The solvent was evaporated under reduced pressure.

Step 4:

Synthesis of 5-Phosphonomethyl-imidazo[1,2-a]pyrimidine-2-carboxylic acid (18)

Ethyl-5-(diethylphosphonomethyl)-imidazo[1,2-a]pyrimidine-2-carboxylic ester (70 mg, 0.2 mole) was dissolved in dichloromethane (5 mL) and trimethylsilyl bromide was added (200 μL, 1.5 mmole). The solution was stirred for 24 hours at room temperature and methanol was added (20 mL). The new solution was let standing at room temperature for one hour, the solvents were evaporated under reduced pressure, the solid residue was suspended in aqueous NaOH (1N, 3 mL) and stirred overnight at room temperature. The solution was neutralized by the addition of aqueous HCl (1N, 3 mL) and poured onto a strongly basic ion-exchange column (OH⁻ form). The column was washed with water and aqueous acetic acid (4N) and the product was eluted with 4N acetic acid. The product was lyophilized (24 mg).

Scheme V (Preparation of Example #2 Compound)

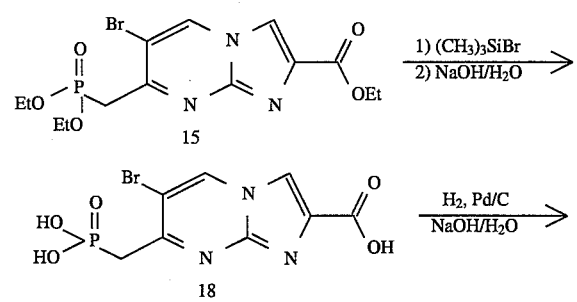

-continued
Scheme V

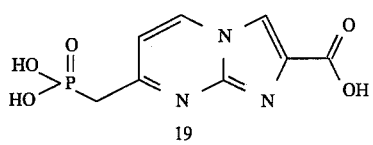

19

EXAMPLE 2

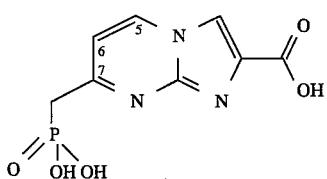

7-phosphonomethyl-imidazo[1,2-a]pyrimidine-2-carboxylic acid (19)]

Step 1:

Synthesis of Ethyl-6-bromo-7-(diethylphosphonomethyl)-imidazo[1,2-a]pyrimidine-2-carboxylic ester (15)

2-Amino-5-bromo-4-(diethylphosphonomethyl)-pyrimidine (0.5 g, 1.7 mole) was suspended in an ethanolic solution of ethyl bromopyruvate (250 uL, 2 mole in 45 mL). The suspension was stirred at room temperature overnight and then brought to reflux for two hours. The solvent was evaporated under reduced pressure, water was added and the solution was made basic by the addition of sodium bicarbonate. The aqueous phase was extracted with dichloromethane (3×20 mL), the organic phase was dried over potassium carbonate and evaporated under reduced pressure. The two isomers 14 and 15 were separated on a silicagel chromatography column eluted with $CH_2Cl_2$-97/EtOH-3. The desired isomer 15 had the longer retention time.

Step 2:

Synthesis of 6-Bromo-7-phosphonomethyl-imidazo[1,2-a]pyrimidine-2-carboxylic acid (18)

Ethyl-6-bromo-7-(diethylphosphonomethyl)-imidazo[1,2-a]pyrimidine-2-carboxylic ester 15 (150 mg, 0.36 mmole) in $CH_2Cl_2$ (5 mL) was mixed with TMSBr (300 μL, 2.27 mmole) and let stand for 2 hours. Methanol (10 mL) was then added. After one hour, the solution was evaporated under reduced pressure. The residue was taken up in 1N NaOH (3 mL) and let stand overnight at room temperature. The solution was neutralized by the addition of 1N HCl (3 mL) and poured onto an ion-exchange column (strongly basic, OH⁻ form), and the column was eluted successively with water, acetic acid (4N), then 1N HCl. The product 18 was eluted with 1N HCl. The appropriate fractions were collected, and lyophilized (21 mg).

Step 3:

Synthesis of 7-phosphonomethyl-imidazo[1,2-a]pyrimidine-2-carboxylic acid (19)

6-Bromo-7-phosphonomethyl-imidazo[1,2-a]pyrimidine-2-carboxylic acid 18 (15 mg) was introduced in a 250 mL Parr bottle with 0.5N NaOH (1 mL), water (15 mL) and Pd on Carbon (5%, 20 mg). The bottle was evacuated, filled with hydrogen and shaken for one hour at room temperature. The product was purified by passing through a strongly basic ion-exchange column. The product 19 was eluted with 1N HCl.

BIOLOGICAL EVALUATION

NMDA-Selective Glutamate Binding Assay

Synaptic plasma membranes (SPM) were prepared as previously described [Monahan, J. B. and Michel, J., "Identification and Characterization of an N-methyl-D-aspartate-specific L[$^3$H]glutamate Recognition Site in Synaptic Plasma Membranes, *J. Neurochem.*, 48, 1699–1708 (1987)]. The SPM were stored at a concentration of 10–15 mg/ml in 0.32M sucrose, 0.5 mM EDTA, 1 mM $MgSO_4$, 5 mM Tris/$SO_4$, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193–197 (1978)]. The SPM were treated identically for the [$^3$H] AMPA (QUIS), [$^3$H]kainate and sodium-dependent L-[$^3$H]-glumatate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times. Prior to use in the NMDAspecific L-[$^3$H]-glutamate binding assay the SPM were thawed, diluted twenty fold with 50 mM Tris/acetate, pH 7.4 containing 0.04% (v/v) Triton X-100, incubated for 30 minutes at 37° C. and centrifuged as described above. The Triton X-100 treated membranes were washed with 50 mM Tris/acetaLe, pH 7.4 and centrifuged at 100,000 g for 15 minutes a total of four times. Triton X-100 treatment of the SPM resulted in a higher affinity and more consistency in this L-[$^3$H]glutamate binding assay. For this reason the $K_d$ for glutamate and the $K_i$ values for other compounds are lower than previously reported; however, the pharmacological profile of this binding site was unaltered. The basic procedure for the receptor subclass binding assays was similar. This general method involved adding the radioligand (12.5 nM L-[$^3$H] glutamate; 0.5 nM [$^3$H]kainate or 10nM [$^3$H]AMPA) to the appropriate concentration of the test compound and initiating the assay by the addition of ice cold synaptic plasma membranes (0.2–0.45 mg). The binding assays were performed in 1.5 mL centrifuge tubes with the total volume adjusted to 1.0 mL. Additions of test compounds were made in 50 mM Tris/acetate, pH 7.4 and incubations were carried out at 0°–4° C. The incubation time for the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents. To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/l acetic acid was then added and the samples counted on a Beckman LS 5800 or 3801 liquid scintillation counter with automatic corrections for quenching and counting efficiency. Nonspecific binding was defined as the residual binding in the presence of either excess L-glutamate (0.1–0.4 mM), kainate (0.01 mM), or NMDA (0.5 mM), and was 15–25% of the total binding in the NMDA binding assay, 19–27% in the AMPA binding assay, 20–30% in the kainate binding assay and 10–15% in the sodium-dependent binding assay. Radioligand binding to the synaptic plasma membranes was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Commuter Appln. Biosci.*, 3, 131 (1987)]. Binding results are reported in Table I for Example compounds of the invention.

[$^3$H]MK-801 Binding assay

Modulation of [$^3$H]MK-801 binding was performed using Triton X-100 (0.04% v/v) treated rat SPM that had been extensively washed. Assay incubations were at 25° C. for 30 min. and contained 5.0 nM [$^3$H]MK-801, L-glutamate (10.0 nM), and various concentrations of the tested compound of the invention in 50 mM Tris/acetate, pH 7.4. The assay was stopped by rapid filtration, using Brandel MB-48 Harvester, through whatman GF/B filters treated with 0.05% polyethylenimine and the samples washed four times with 2.0 mL cold buffer. The radioactivity associated with the filter was determined by liquid scintillation spectrometry. Nonspecific binding was defined using 60 μM MK-801. $IC_{50}$ were determined using a logit-log transformation of the binding data. Results are reported in Table 1.

TABLE I

| | Receptor Binding Data ($IC_{50}$) | |
|---|---|---|
| Compound Ex. # | [$^3$H]GLU $K_i$ (μM) | [$^3$H]MK-801 $K_i$ (μM) |
| 1 | 8.8 | 4.6 |
| 2 | 14% inhibition @ 10 μM | NT |

NT = Not Tested

Forebrain Ischemia Assay

This assay is used to determine the extent of protection afforded by compound of the invention to neural brain cells subjected to ischemic conditions. Male Mongolian gerbils, 50–70 gm, are used as subjects. Compound of the invention is injected i.p. 30 minutes prior to carotid occlusion into 6 gerbils at two different doses (300 mg/kg and 500 mg/kg). In preparation for surgical procedures, the animals are lightly anesthetized with methoxyflurane and placed upside down on a heated pad with their snout within a nosecone. A 70:30 mixture of nitrous oxide and oxygen containing 0.5% halothane is circulated through the nosecone to provide continuous anesthesia throughout the surgical procedure. Amidline incision is made in the neck and the carotid arteries are exposed. A length of suture thread is placed under each carotid. The thread is then tightened around each carotid and pressure applied to the thread to insure flow is occluded. Flow is occluded for 4–5 minutes and then the thread is removed. The carotids are visually inspected to confirm that fellow has occurred. The wound is then closed with autoclips and the gerbils allowed to recover. Following surgery, the gerbils are kept alive for 7 days. They are anesthetized with 100 mg/kg sodium pentobarbital and perfused transcardially with saline (with heparin) followed by buffered formalin. The brain is removed, trimmed and prepared for histological processing. Sections (10 microns) are stained with thionin. At 7 days following this type of transient global forebrain ischemia, damaged neurons in the vulnerable CA1 region of the hippocampus will have degenerated and have been cleared away by glia. Quantification of the resulting lesion is made by counting the pyramidal cell somata in a 0.5 mm length of CA1 of the hippocampus on the section corresponding to P 1.7mm in the gerbil brain atlas. Normal cell count in this region of the hippocampus in unoperated gerbils is 146±2. The effects of compound of the invention are assessed by comparing the number of neural cells found in the hippocampus of subjects treated with of the invention compound with the cell number found in the appropriate control groups. The groups are compared by the Mann-Whitney U test [*Elementary Applied Statistics*, Wiley and Sons, New York (1965)]. It is expected that cell loss would be significantly reduced in gerbils given compound of the invention as compared to an untreated control animal.

Administration of compounds within Formula I to humans can be by any technique capable of introducing the compounds into the bloodstream of a human patient, including oral administration, and by intravenous, intramuscular and subcutaneous injections.

Compounds indicated for prophylacmic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. various equivalents, changes and modifications may be made without departing from the spirit and scope of this invention, and it is understood that such equivalent embodiments are part of this invention.

What is claimed is:

1. A method for treating neurotoxic injury resulting from ischemia, which method comprises treating a subject susceptible to neurotoxic injury with a therapeutically effective amount of an antagonist compound of Formula I:

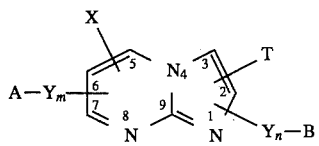

wherein A is selected from

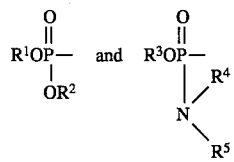

wherein B is selected from

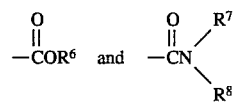

wherein each of $R^1$ through $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

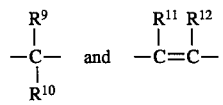

with the proviso that the total number of carbon atoms in each of $Y_m$ or $Y_n$ cannot exceed twenty carbon atoms; wherein each of $R^9$ and $R^{10}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein each of $R^{11}$ and $R^{12}$ is independently selected from hydrido, alkyl, haloalkyl, phenyl, hydroxyalkyl and alkoxyalkyl; wherein each of m and n is a number independently selected from zero to four, inclusive;

wherein X is one or more groups attachable at one or more of the 5-, 6- and 7-ring positions of the imidazo [1,2-a]pyrimidine ring system; wherein each X and T is independently selected from hydrido, halo, alkyl, cycloalkyl, cycloalkylalkyl, haloalkyl, alkenyl having two to about twenty carbon atoms and having one carbon-carbon double bond, alkynyl having two to about twenty carbon atoms and having one carbon-carbon triple bond, phenyl, benzyl, hydroxy, hydroxyalkyl, alkoxy, phenoxy, alkoxyalkyl, benzyloxy, cyano, alkanoyl, alkylthio and arylthio,

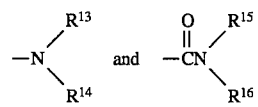

wherein each of $R^{13}$, $R^{14}$, $R^{15}$ and $R^{16}$ is independently selected from hydrido, alkyl and phenyl; or a pharmaceutically-acceptable salt thereof.

2. The method of claim 1 wherein said antagonist compound is selected from compounds of Formula II:

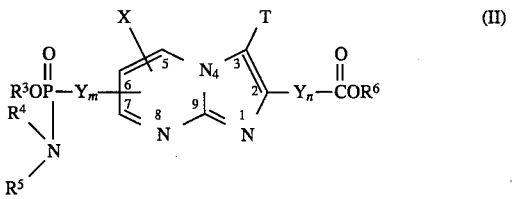

wherein each of $R^3$, $R^4$, $R^5$ and $R^6$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

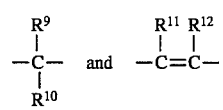

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the tetrahydroimidazo[1,2-a]pyrimidine ring system; wherein each X and T is independently selected from hydrido, halo, alky, cycloalkyl, cycloalkylalkyl, haloalkyl, alkenyl having two to about twenty carbon atoms and having one carbon-carbon double bond, alkynyl having two to about twenty carbon atoms and having one carbon-carbon triple bond, phenyl, benzyl, hydroxy, hydroxyalkyl, alkoxy, phenoxy, alkoxyalkyl, benzyloxy, cyano, alkanoyl, alkylthio and arylthio,

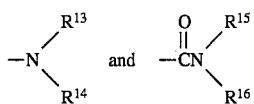

wherein each of $R^{13}$, $R^{14}$, $R^{15}$ and $R^{16}$ is independently selected from hydrido, alkyl and phenyl;

or a pharmaceutically-acceptable salt thereof.

3. The method of claim 2 wherein said antagonist compound is selected from compounds, and their pharmaceutically-acceptable salts, of the group of compounds consisting of ethyl 5-[(ethoxyphosphonamide)methyl]-imidazo[1,2-a]pyrimidine-2-carboxylate;
5-(phosphonamidemethyl)-imidazo[1,2-a]pyrimidine-2-carboxylic acid;
ethyl 6-[(ethoxyphosphonamide)methyl]-imidazo[1,2-a]-pyrimidine-2-carboxylate;
6-(phosphonamidemethyl)-imidazo[1,2-a]pyrimidine-2-carboxylic acid;
ethyl 7-[(ethoxyphosphonamide)methyl]-imidazo[1,2-a]pyrimidine-2-carboxylate;
7-(phosphonamidemethyl)-imidazo[1,2-a]pyrimidine-2-carboxylic acid;
ethyl 6-chloro-5-[(ethoxyphosphonamide)methyl]-imidazo[1,2-a]pyrimidine -2-carboxylate;
6-chloro-5-(phosphonamidemethyl)-imidazo[1,2-a]pyrimidine-2-carboxylic acid;
ethyl 7-chloro-5-[(ethoxyphosphonamide)methyl]-imidazo[1,2-a]pyrimidine-2-carboxylate;
7-chloro-5-(phosphonamidemethyl)-imidazo[1,2-a]pyrimidine-2-carboxylic acid;
ethyl 5-(ethoxyphosphonamide)-imidazo[1,2-a]pyrimidine-2-carboxylate;
ethyl 5-(ethoxyphosphonamide)-imidazo[1,2-a]pyrimidine-2-carboxylate, monohydrochloride;
5-phosphonamide-imidazo[1,2-a]pyrimidine-2-carboxylic acid; ethyl 5-[2-(ethoxyphosphonamide)-E-ethenyl]-imidazo[1,2-a]pyrimidine-2-carboxylate;
5-(2-phosphonamide-E-ethenyl)-imidazo[1,2-a]pyrimidine-2-carboxylic acid; and
5-(2-phosphonamideethyl)-imidazo[1,2-a]pyrimidine-2-carboxylic acid.

4. The method of claim 1 wherein said antagonist compound is selected from compounds of Formula III:

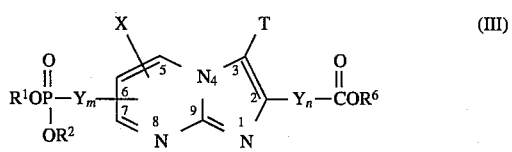

wherein each of $R^1$, $R^2$ and $R^6$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

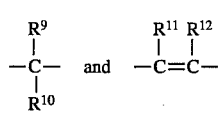

with the proviso that the total number of carbon atoms in each of $Y_m$ or $Y_n$ cannot exceed ten carbon atoms;

wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl having two to about twenty carbon atoms and having one carbon-carbon double bond, alkynyl having two to about twenty carbon atoms and having one carbon-carbon triple bond, phenyl, benzyl, hydroxy, hydroxyalkyl, alkoxy, phenols, alkoxyalkyl, benzyloxy, cyano, alkanoyl, alkylthio and arylthio,

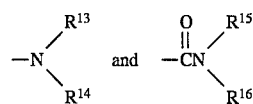

wherein each of $R^{13}$, $R^{14}$, $R^{15}$ and $R^{16}$ is independently selected from hydrido, alkyl and phenyl;

or a pharmaceutically-acceptable salt thereof.

5. The method of claim 4 wherein said antagonist compound is selected from compounds, and their pharmaceutically-acceptable salts, of the group of compounds consisting of ethyl 5-[(diethoxyphosphinyl)methyl]-imidazo[1,2-a]pyrimidine-2-carboxylate;
5-(phosphonomethyl)-imidazo[1,2-a]pyrimidine-2-carboxylic acid;
ethyl 6-[(diethoxyphosphinyl)methyl]-imidazo[1,2-a]pyrimidine-2-carboxylate;
6-(phosphonomethyl)-imidazo[1,2-a]pyrimidine-2-carboxylic acid;
ethyl 7-[(diethoxyphosphinyl)methyl]-imidazo[1,2-a]pyrimidine-2-carboxylate;
7-(phosphonomethyl)-imidazo[1,2-a]pyrimidine-2-carboxylic acid;
ethyl 6-chloro-5-[(diethoxytphosphinyl)methyl]-imidazo[1,2-a]pyrimidine-2-carboxylate;
6-chloro-5-(phosphonomethyl)-imidazo[1,2-a]pyrimidine-2-carboxylic acid;
ethyl 7-chloro-5-[(diethoxyphosphinyl)methyl]-imidazo[1,2 a]pyrimidine-2-carboxylate;
7-chloro-5-(phosphonomethyl)-imidazo[1,2-a]pyrimidine-2-carboxylic acid;
ethyl 5-(diethoxyphosphinyl)-imidazo[1,2-a]pyrimidine-2-carboxylate;
ethyl 5-(diethoxyphosphinyl)-imidazo[1,2-a]pyrimidine-2-carboxylate, monohydrochloride;
5-phosphono-imidazo[1,2-a]pyrimidine-2-carboxylic acid; ethyl 5-[2-(diethoxyphosphinyl)-E-ethenyl]-imidazo[1,2-a]pyrimidine-2-carboxylate;
5-(2-phosphono-E-ethenyl)-imidazo[1,2-a]pyrimidine-2-carboxylic acid; and
5-(2-phosphonoethyl)-imidazo[1,2-a]pyrimidine-2-carboxylic acid.

6. The method of claim 5 wherein said antagonist compound is 5-phosphonomethyl-imidazo[1,2-a]pyrimidine-2-carboxylic acid or a pharmaceutically-acceptable salt thereof.

7. The method of claim 5 wherein said antagonist compound is 7-phosphonomethylimidazo[1,2-a]pyrimidine-2-carboxylic acid or a pharmaceutically-acceptable salt thereof.

8. The method of claim 1 wherein said antagonist compound is selected from compounds of Formula IV:

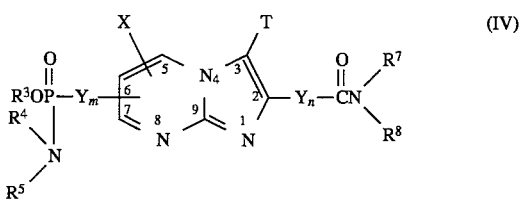

wherein each of $R^3$, $R^4$, $R^5$, $R^7$ and $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

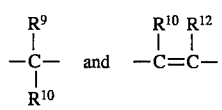

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl having two to about twenty carbon atoms and having one carbon-carbon double bond, alkynyl having two to about twenty carbon atoms and having one carbon-carbon triple bond, phenyl, benzyl, hydroxy, hydroxyalkyl, alkoxy, phenoxy, alkoxyalkyl, benzyloxy, cyano, alkanoyl, alkylthio and arylthio,

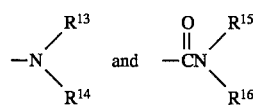

wherein each of $R^{13}$, $R^{14}$, $R^{15}$ and $R^{16}$ is independently selected from hydrido, alkyl and phenyl;
or a pharmaceutically-acceptable salt thereof.

9. The method of claim 8 wherein said antagonist compound is selected from compounds, and their pharmaceutically-acceptable salts, of the group of compounds consisting of 5-[(ethoxyphosphonamide)methyl]-imidazo[1,2-a]pyrimidine-2-carboxamide;

5-(phosphonamidemethyl)-imidazo[1,2-a]pyrimidine-2-carboxamide;

6-[(ethoxyphosphonamide)methyl]-imidazo[1,2-a]pyrimidine-2-carboxamide;

6-(phosphonamidemethyl)-imidazo[1,2-a]pyrimidine-2-carboxamide;

7-[(ethoxyphosphonamide)methyl]-imidazo[1,2-a]pyrimidine-2-carboxamide;

7-(phosphonamidemethyl)-imidazo[1,2-a]pyrimidine-2-carboxamide;

6-chloro-5-[(ethoxyphosphonamide)methyl]-imidazo[1,2-a]pyrimidine-2-carboxamide;

6-chloro-5-(phosphonamidemethyl)-imidazo[1,2-a]pyrimidine-2-carboxamide;

7-chloro-5-[(ethoxyphosphonamide)methyl]-imidazo[1,2-a]pyrimidine-2-carboxamide;

7-chloro-5-(phosphonamidemethyl)-imidazo[1,2-a]pyrimidine-2-carboxamide;

5-(ethoxyphosphonamide)-imidazo[1,2-a]pyrimidine-2-carboxamide;

5-(ethoxyphosphonamide)-imidazo[1,2-a]pyrimidine-2-carboxamide, monohydrochloride;

5-phosphonamide-imidazo[1,2-a]pyrimidine-2-carboxamide;

5-[2-(ethoxyphosphonamide)-E-ethenyl]-imidazo[1,2-a]pyrimidine-2-carboxamide;

5-(2-phosphonamide-E-ethenyl)-imidazo[1,2-a]pyrimidine-2-carboxamide; and 5-(2-phosphonamideethyl)-imidazo[1,2-a]pyrimidine-2-carboxamide.

10. The method of claim 1 wherein said antagonist compound is selected from compounds of Formula V:

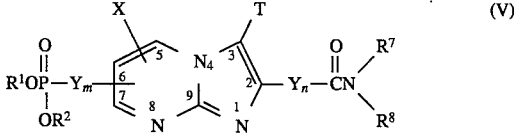

wherein each of $R^1$, $R^2$, $R^7$ and $R^8$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

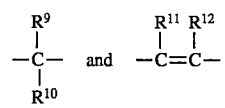

with the proviso that the total number of carbon atoms in each of $Y_m$ or $Y_n$ cannot exceed ten carbon atoms; wherein each of $R^9$ and $R^{10}$ is independently selected from hydrido, alkyl, cycloalkyl, halo, haloalkyl, hydroxy, hydroxyalkyl, alkoxy, alkoxyalkyl and alkanoyl; wherein each of $R^{11}$ and $R^{12}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the imidazo[1,2-a]pyrimidine ring system; wherein each X and T is independently selected from hydrido, halo, alkyl, cycloalkyl, cycloalkylalkyl, haloalkyl, alkenyl having two to about twenty carbon atoms and having one carbon-carbon double bond, alkynyl having two to about twenty carbon atoms and having one carbon-carbon triple bond, phenyl, benzyl, hydroxy, hydroxyalkyl, alkoxy, phenoxy, alkoxyalkyl, benzyloxy, cyano, alkanoyl, alkylthio and arylthio,

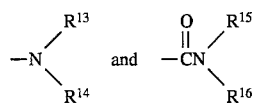

wherein each of $R^{13}$, $R^{14}$, $R^{15}$ and $R^{16}$ is independently selected from hydrido, alkyl and phenyl;
or a pharmaceutically-acceptable salt thereof.

11. The method of claim 10 wherein said antagonist compound is selected from compounds, and their pharmaceutically-acceptable salts, of the group of compounds consisting of
5-[(diethoxyphosphinyl)methyl]-imidazo[1,2-a]pyrimidine-2-carboxamide;
5-(phosphonomethyl)-imidazo[1,2-a]pyrimidine-2-carboxamide;
6-[(diethoxyphosphinyl)methyl]-imidazo[1,2-a]Pyrimidine-2-carboxamide;
6-(phosphonomethyl)-imidazo[1,2-a]pyrimidine-2-carboxamide;
7-[(diethoxyphosphinyl)methyl]-imidazo[1,2-a]pyrimidine-2-carboxamide;
7-(phosphonomethyl)-imidazo[1,2-a]pyrimidine-2-carboxamide; 6-chloro-5-[(diethoxyphosphinyl)methyl]-imidazo[1,2-a]pyrimidine - 2- carboxamide;
6-chloro-5-(phosphonomethyl)-imidazo[1,2-a]pyrimidine-2-carboxamide;
7-chloro-5-[(diethoxyphosphinyl)methyl]-imidazo[1,2-a]pyrimidine - 2- carboxamide;
7-chloro-5-(phosphonomethyl)-imidazo[1,2-a]pyrimidine-2-carboxamide;
5-(diethoxyphosphinyl)-imidazo[1,2-a]pyrimidine-2-carboxamide;
5-(diethoxyphosphinyl)-imidazo[1,2-a]pyrimidine-2-carboxamide, monohydrochloride;
5-phosphono-imidazo[1,2-a]pyrimidine -2-carboxamide;
5-[2-(diethoxyphosphinyl)-E-ethenyl]-imidazo[1,2-a]pyrimidine - 2-carboxamide;
5-(2-phosphono-E-ethenyl)-imidazo[1,2-a]pyrimidine-2-carboxamide; and
5-(2-phosphonoethyl)-imidazo[1,2-a]pyrimidine-2-carboxamide.

* * * * *